United States Patent
Bouchon-Meunier et al.

(10) Patent No.: US 8,350,906 B2
(45) Date of Patent: Jan. 8, 2013

(54) CONTROL METHOD BASED ON A VOLUNTARY OCULAR SIGNAL PARTICULARLY FOR FILMING

(75) Inventors: Bernadette Bouchon-Meunier, Paris (FR); Yves Pupulin, Paris (FR); Thierry Baccino, Nice (FR); Charles Tijus, Paris (FR)

(73) Assignees: Binocle, Bry sur Marne (FR); Universite Pierre et Marie Curier (Paris 6), Paris cedex (FR); Universite Paris VIII, Saint Denis Cedex (FR); Centre National de la Recherche Scientifique, Paris (FR)

( * ) Notice: Subject to any disclaimer, the term of this patent is extended or adjusted under 35 U.S.C. 154(b) by 619 days.

(21) Appl. No.: 12/525,258
(22) PCT Filed: Jan. 30, 2008
(86) PCT No.: PCT/FR2008/000106
§ 371 (c)(1), (2), (4) Date: Dec. 3, 2009
(87) PCT Pub. No.: WO2008/107564
PCT Pub. Date: Sep. 12, 2008

(65) Prior Publication Data
US 2010/0118141 A1    May 13, 2010

(30) Foreign Application Priority Data
Feb. 2, 2007    (FR) .................................... 07 00754

(51) Int. Cl.
H04N 7/18    (2006.01)
H04N 5/253    (2006.01)
(52) U.S. Cl. .......................................... 348/135; 348/78
(58) Field of Classification Search .................. None
See application file for complete search history.

(56) References Cited

U.S. PATENT DOCUMENTS

| | | | |
|---|---|---|---|
| 4,109,145 A | 8/1978 | Graf | |
| 5,583,795 A | 12/1996 | Smyth | |
| 5,689,619 A | 11/1997 | Smyth | |
| 5,717,413 A | 2/1998 | Mizouchi | |
| 5,751,260 A | 5/1998 | Nappi et al. | |
| 5,790,099 A | 8/1998 | Okada | |
| 6,091,378 A * | 7/2000 | Richardson et al. | 345/7 |
| 6,152,563 A * | 11/2000 | Hutchinson et al. | 351/209 |
| 7,641,341 B2 * | 1/2010 | Weinblatt | 351/210 |
| 2002/0180799 A1 | 12/2002 | Peck et al. | |
| 2006/0098087 A1 * | 5/2006 | Brandt et al. | 348/61 |

FOREIGN PATENT DOCUMENTS
EP    1 168 830 A1    6/2000

* cited by examiner

Primary Examiner — John B. Walsh
(74) Attorney, Agent, or Firm — Morgan, Lewis & Bockius LLP

(57) ABSTRACT

The invention relates to a control method based on a controlling eye signal, the method being characterized in that it comprises the following steps: detecting at least one slow movement corresponding to an eye movement of at least one eye of an operator; generating a said eye control signal from at least one detected slow movement; and producing a command from the eye control signal. The invention applies in particular to controlling cameras by eye.

24 Claims, 3 Drawing Sheets

$y = 762.469 - .626 * x; R^2 = .124$

CONTROL METHOD BASED ON A VOLUNTARY OCULAR SIGNAL PARTICULARLY FOR FILMING

RELATED APPLICATIONS

The present application is a U.S. National Phase Application of International Application PCT/FR2008/000106, filed Jan. 30, 2008, which claims the benefit of French application No. 07/00754, filed Feb. 2, 2007, all of which are herein incorporated by reference in their entirety.

BRIEF SUMMARY OF THE INVENTION

The present invention relates to a control method based on an eye signal, in particular a method suitable for use in controlling a picture-taking device having at least one real or virtual camera.

BACKGROUND OF THE INVENTION

Eye movements are movements of small amplitude (1 to 25 minutes of arc), of very short duration (0.01 seconds (s) to 0.05 s) and that have an angular speed that may be as great as 500 degrees per second (°/s). Video cameras have been used for more than ten years to monitor eye movements and to track them. Analyzing the track of the eye by processing eye data makes it possible to identify eye movements of involuntary nature as constituted by micro-movements of the eye (nystagmus), slow drifts of gaze, blinking, eye movements of a voluntary nature (changing the XY coordinates of the gaze position of the eye on the screen), movement speed, saccade amplitudes, gaze fixes, and the durations thereof, and vergence movements.

Collecting and analyzing eye movements by means of an eye tracker, preceded by necessary calibration in order to determine the XY coordinates of the position of the gaze on the screen, have become very reliable, fast, and accurate. They make it possible in real time to obtain the track followed by the eye when inspecting the content of a screen, in particular to study the amount of attention given to components in a visual scene.

The advantages of eye control, for devices were identified very early (Ware & Mikaelien, "An evaluation of an eye tracker as a device for computer input", CHI+GI, 1987, Conference Proceedings, SIGHI Bulletin ACM, p. 183-188), for military applications (e.g. Smyth, Bates, Lopez, & Ware, "A comparison of eye-gaze to touch panel and head fixed reticule for helicopter display control"—Proceeding of the 2nd Mid-Atlantic Human Factors Conference, 1994, p. 49 et seq.), for man-machine interactions (e.g. R J K Jacob, "The use of eye movements in human-computer interaction techniques—what you look is what you get", ACM Transactions on Information Systems 1991, 9(3), pp. 152-169), for remote control (e.g.: project of the "IBM Almaden Research Center"), or for robot control (e.g.: Atienza & Zelinsky, 2003 "Interactive skills using active gaze tracking", Proceedings of the 5th International Conference on Multimodal Interfaces, Vancouver, Canada, pp. 188-195).

When in operation, in particular for controlling pointing and direction, eye movement is faster than control by moving articles because it is more direct, (work of the "Gaze-based interaction group").

Thus, a high-resolution camera placed at two meters from a person can track the movements of that person's retina and convert them into eye commands. There already exist:

devices for inputting alphabetical characters by analyzing eye gazes on digital keyboards;

more highly integrated gaze-control devices (managing emails, writing text, such as the "Eye-gaze interaction" project and the "Visuoboard" system); and devices for analyzing behavior on articles (filmed by camera) coupled with analysis of gaze tracking (Atienza & Zelinsky, 2003).

All of those devices rely on the principle of analyzing a gaze fixed on a zone of the screen ("location-based interaction") and of positioning the cursor when a fixed gaze is detected. A command is then given by blinking, by hand (clicking a mouse), or by maintaining a gaze for a long duration, e.g. to perform a zoom or to open a menu, in association with the duration of a gaze ("time-based interaction").

That principle does not enable continuous control to be provided, as is needed for implementing functions of controlling a real or virtual camera (zooming, camera movements, . . . ).

Eye movements and software for analyzing gaze tracks present three characteristics that explain why eye control has until now been limited to eye commands that do not involve continuous movement of the eye for control purposes. Eye control has relied on icons ("location-based interaction"), on buttons, or on locations that are well defined.

A first characteristic is that the eye senses information but does not produce it. When the eyes form part of a control system, it is necessary to distinguish between actions that amount to sensing information and actions that should be taken as commands. Any failure (producing a command when the user is looking, or considering that the user is looking when in fact the user is seeking to issue a command) makes the control system unreliable and difficult to use. For example, a command may be issued by gazing for a sufficient length of time and then blinking the eyelids.

The second characteristic is that the eyes are continuously in movement (micro-movements such as nystagmuses up to saccades of the eye of various amplitudes). It is therefore necessary to distinguish between what counts as a gaze and what counts as a movement of the eye. All software for analyzing eye data does this by aggregating gaze positions that are close together in space and in time. This thus defines zones that correspond to fixed gazes.

A third characteristic is that the analysis software outputs only gazes that are fixed (in terms of location and duration) and saccades (locating the start, locating the finish, providing the amplitude and the duration). Slow and oriented movements of gaze in some particular direction are ignored by the analysis software.

Whether performed mechanically or under software control, camera control always involves movement, such that it is necessary to control the camera by hand as well as by looking at what is being filmed.

There does not exist any eye movement control system for taking two-dimensional (2D), XY pictures even though such a system would present undeniable advantages. Amongst the advantages, mention can be made of the possibility of hands-free control, and above all of controlling the shooting of an image from the image itself, in which the natural way of inspecting the visual scene is applied to taking pictures thereof. For example, such a device would enable a film director with a viewfinder and a monitor screen to work directly on shooting from a monitor screen of large size. Such a large-sized screen presents three advantages:

greater freedom of movement for the gaze of the operator;
greater accuracy in analyzing the detection of eye movement; and
the operator observing the image at a size that is closer to its final size.

The idea on which the present invention is based is to use gaze as a control system, in particular for controlling a real or virtual 2D and/or three-dimensional (3D) camera by analyzing slow and oriented movements of gaze.

The invention thus provides a control method based on a controlling eye signal, and it is characterized by the following steps:

detecting at least one slow movement corresponding to an eye movement of at least one eye of an operator;
generating a said eye control signal from at least one detected slow movement; and
producing a command from the eye control signal.

Advantageously, said slow movement corresponds to a regular angular movement of the eye at an angular speed lying in the range 1°/s to 40°/s, particularly in the range 1°/s to 30°/s, and more particularly in the range 5°/s to 20°/s.

Slow movement may be detected by determining its path, in particular its direction, by means of a calculation method, in particular by means of linear regression.

The detection of a saccade (or fast movement) and/or a fixed gaze may give rise to an interruption in the generation of the control signal.

The eye control signal may be a function (an increasing or decreasing function) of the angular movement of the eye. The eye control signal may represent the position of the eye and/or the speed of the slow movement of the eye and/or its direction. In this way, as soon as a slow movement is detected, all of the parameters of the slow movement can be used for generating a continuous command, its start, and/or its end.

At least one control parameter, e.g. a speed, may be a function of at least one eye movement parameter, e.g. its speed and/or its direction.

By way of example, giving a command may consist in making a selection between options. The options may be organized in a continuum or as discrete values as a function of at least one eye movement parameter. For example, so long as the slow movement continues, the choice remains open, and stopping the slow movement or interrupting it over a duration that is greater than a selected threshold determines the choice.

The beginning and/or the end of a command may be generated by the beginning and/or the end of an eye control signal, or indeed by a command given by voice, by eye, and/or by hand.

In a first variant, the type of control to which the eye control signal is allocated is determined by at least one parameter of the eye movement, e.g. its direction.

In a second variant, the type of control to which the eye control signal is allocated is determined by a command given by voice, by eye, or by hand.

The eye control signal may also be an on/off signal.

The invention is particularly adapted to remotely controlling picture-taking by on-board cameras or by cameras on hinged arm booms that are in very widespread use because of the effect they achieve, remote surveillance cameras, and also performing remote actions involving manipulating tools remotely. When manipulation is to be performed remotely, there are two systems to be controlled by hand: the camera (if it is desired to act on picture-taking) and the controlled instrument. The invention makes it possible to control the camera by gaze and to control the instrument by hand.

The invention applies in particular to controlling at least one real or virtual camera by eye.

The type of control to which the control signal is allocated may for example be starting to shoot and/or changing a zoom and/or adjusting aperture and/or adjusting focusing and/or rotating the camera about its own axis (rolling), and/or moving the camera ("traveling"), and/or (in a stereoscopic system) varying the spacing between the axes and/or varying vergence. The particular command may be determined by giving a command by voice (voice and/or eye control (fixing gaze on an icon, blinking, . . . ) and/or by hand (keyboard, mouse, joystick, etc.) or indeed by an angular movement parameter, e.g. direction).

The method of the invention may be characterized in that it includes a prior training procedure performed by an operator. This procedure is based on:

analyzing eye position data in successive same-duration T time windows, and classifying data sets for each window in at least two classes; namely
a slow movement class in which a data set comprises sequential data points of values that are close to one another and that are organized in a continuous geometrical pattern, e.g. a segment having a slope; and
otherwise a class of non-slow movements.

Depending on the selected mode, the class of non-slow movements comprises two sub-classes:

a fixed gaze sub-class, else an eye saccade sub-class defined in particular by an acceleration peak followed by strong deceleration.

BRIEF DESCRIPTION OF THE DRAWINGS

Other characteristics and advantages of the invention appear better on reading the following description with reference to the drawings, in which.

DETAILED DESCRIPTION OF THE INVENTION

The invention makes use of producing, collecting, and processing slow and oriented voluntary movements of the eyes that are produced with slowness and orientation that the gaze does not present under natural conditions of inspecting visual scenes. Nevertheless, such slowness and orientation (that are easily detected), are to be found during involuntary downward drift of the eye while not inspecting a scene. These are so-called "slow" movements of the order of 1°/s to 40°/s that are ignored by gaze-tracking software since they correspond neither to fixations, nor to saccades. Producing such slow movements, when the eye is not tracking a target, requires training: people without training do not manage, they produce saccades (cf. Richard J. Krauzlis "Recasting the smooth pursuit eye movement system", Journal of Neurophysiology 91: pp. 591-603, 2004, in particular at page 599).

According to the invention, slow and oriented movements (specifically micro-saccades that cause the eye to move in the same direction) are extracted by a data analysis method. This extraction makes it possible to distinguish between active intentional movements for acting on the camera, and natural passive tracking movements. The analysis is associated with adapting to the user in order to incorporate the user's physiological and behavior particularities.

Figure 1:
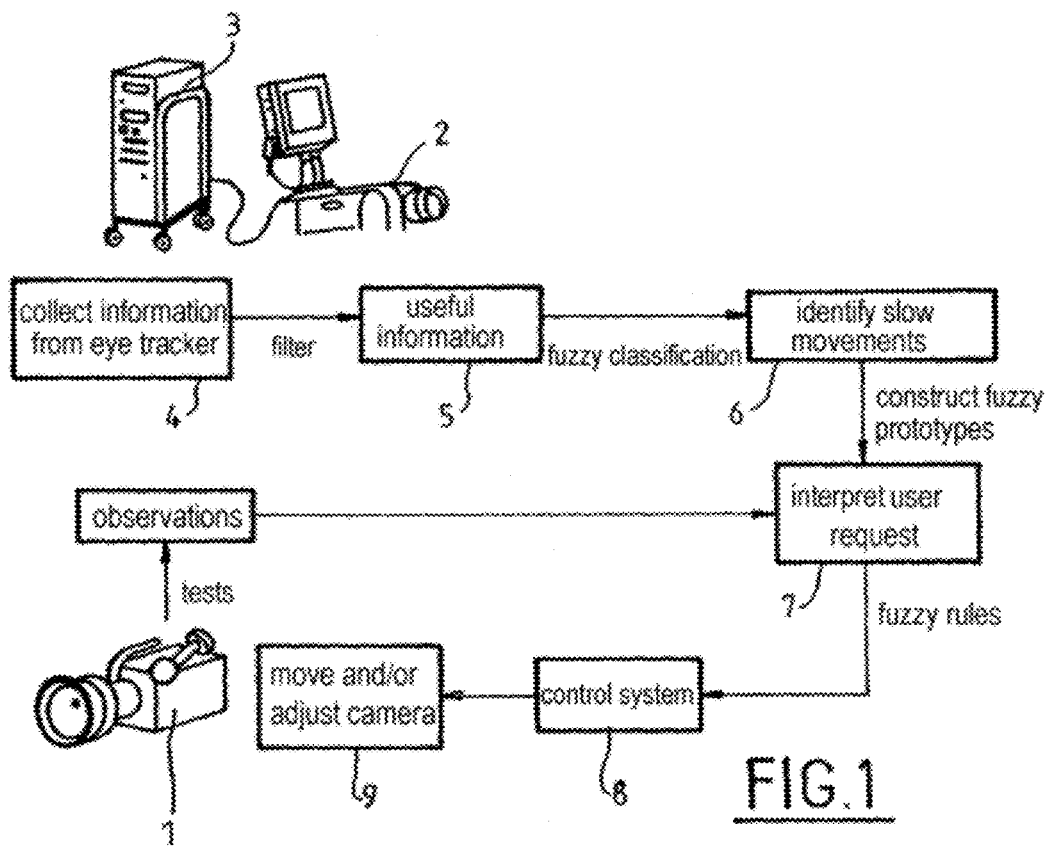
FIG. 1 shows the operation of eye control applied to a video camera.

The system shown in FIG. 1 comprises a camera 1, an eye tracker 2, and an installation 3 for collecting information from the eye tracker. This information is collected at 4. After filtering, the useful information is stored at 5, and then classified at 6 in order to identify slow movements. At 7, a correspondence table serves to interpret the identified slow movements in order to generate a command at 8, thereby producing signals at 9 for moving and/or adjusting the camera.

The method is as follows:

1) Basic equipment including an eye tracker is itself known. The eye tracker delivers the XY coordinates of the gaze position on the screen where the pictures being taken by the camera are displayed, and it also produces the vergence values for the two eyes.

2) A calibration stage having the following purposes:
   a. adjusting the recording of the position of each of the eyes relative to predefined XY positions on the screen; and
   b. making the vergence of the eyes correspond to depth positions when performing 3D eye tracking, for controlling 3D cameras.

The idea is to fix successive points (crosses) appearing at equal distances on the screen. These points define the 2D or 3D calibration grid XY or XYZ. The values recorded during calibration (coordinates of the eye for predefined positions) are used during data analysis to project the position of the eye geometrically at each instant into the XY plane of the screen, or for controlling 3D cameras, into the XYZ space.

Figure 2:
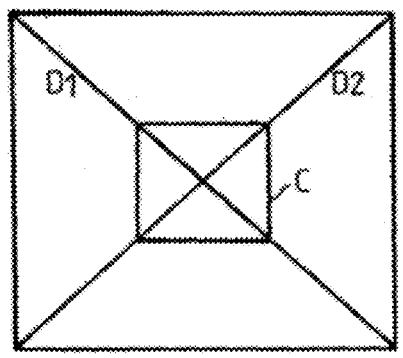
FIG. 2 shows a shooting view-finder.

3) Displaying on the screen not only the image of the pictures being taken, but also two diagonals D1 and D2 and a centered frame C (FIG. 2).

4) The controls for the 2D or 3D camera are displayed on the screen in the form of icons:
   i. controls associated with the picture-taking optics (zoom, focus, aperture);
   ii. controls associated with pivoting movements of cameras (horizontal panning, or vertical tilting, or rolling about the axis of the camera, together with combinations thereof, and traveling movements that may be lateral, vertical, or along the axis, and combinations thereof); and
   iii. with a 3D camera, controls associated with adjusting relief parameters for depth (spacing between axes and vergence).

5) Fixing the eye in a zone that corresponds to a control or a combination of controls, thereby activating said control or said combination of controls. The icon(s) corresponding to the activated control(s) is/are displayed in inverse video to indicate that the slow gaze movements that are going to be recorded will correspond to that control.

6) Successive XY and XYZ coordinate that are analyzed in terms of proximity and direction. Data analysis techniques are used that are based on training to determine in real time whether the successive coordinates relate to a saccade (coordinates far apart), to a fixed gaze (coordinates close together and no direction), or to a slow movement of the gaze (coordinates close and in some approximate direction).

7) A correspondence table for each camera control that enables the value of the control to be determined (e.g. forwards or backwards for the zoom control) on the basis of the category of the identified direction (increasing X value: zoom forwards, decreasing X value: zoom backwards), in the context of limits on value variations, which limits can be set and are associated with each control.

8) A control value (e.g. "zoom forwards") is sent to the mechanics of the camera in association with a speed value that is proportional to the slow movement of the gaze.

9) Identifying a large saccade or a gaze that is fixed, thereby bringing the command to an end, except for the "picture-taking" command. An undo control serves to return to an initial state preceding the performance of a command.

10) The conditions under which the method are performed are as follows:
   a. each control is subject to settings. The user determines the relationship between the speed of execution of the control and the slow movements of the gaze; and
   b. each control is adaptable. The system takes account of successes and failures in the execution of commands.

11) A training stage that enables the settings of the device to be set and that enables it to adapt to the user.

Pictures may also be taken stereoscopically, using two or N cameras to correspond to the retinal disparity of binocular vision, with reproduction being by means of appropriate apparatus (by anaglyphic selection, by linear and circular polarization, on an auto-stereoscopic screen, using an image depth map ("Zmap"), by menus of an "augmented 2D" viewing system, or by any other system for reproducing relief or volume of the holographic type.

Implementing Eye Control for Directing a Movement of a 2D Camera in the Plane of the Lens Step 1—Selecting the "Take Pictures" Function The "take pictures" function is activated either by pressing on a keyboard key, or by causing the eye on the zone of a "take pictures" button, or indeed by issuing a command by voice. The "take pictures" button is displayed in inverse video, indicating that it is active. This means that the initialization device is engaged: from this moment on, slow movements and their directions will control the camera.

Step 2—In-Line Data Analysis: Detecting Slow Movement by the Non-Supervised or Semi-Supervised Training Technique The base data comprises the XY positions of the left eye (L) and of the right eye (R) on the screen, as output by the eye tracker, and as sampled once every 20 ms (T) as in Table 1 below.

TABLE I

Raw eye data

| Reference | T | X(L) | Y(L) | X(R) | Y(R) |
| --- | --- | --- | --- | --- | --- |
| 1 | 19 | 506 | 376 | 520 | 376 |
| 2 | 39 | 501 | 381 | 521 | 372 |
| 3 | 59 | 502 | 378 | 515 | 372 |
| 4 | 79 | 502 | 379 | 516 | 370 |
| 5 | 99 | 505 | 385 | 516 | 391 |
| 6 | 118 | 507 | 377 | 512 | 380 |
| 7 | 138 | 502 | 384 | 518 | 372 |

Figure 3:
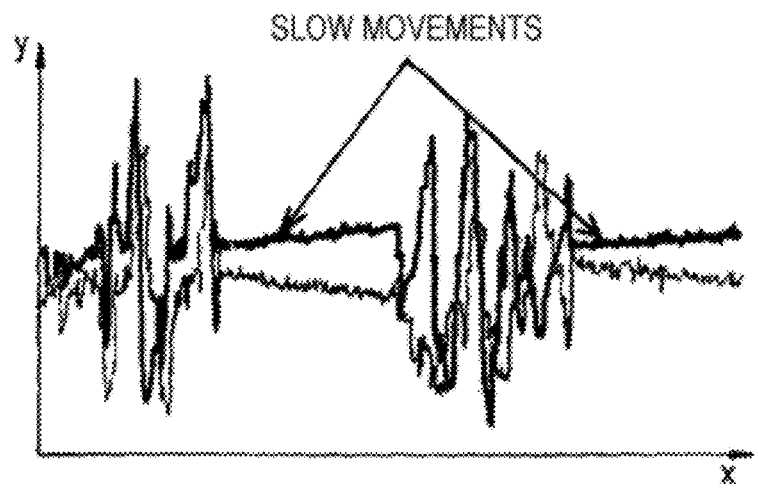
FIG. 3 shows basic eye data for two slow movements preceded and separated by movements that are not slow. 4000 successive positions of the eyes are plotted along the abscissa. This data is sampled once every 20 milliseconds (ms), giving a recording with a duration of 80 s.

The problem to be solved consists in identifying quickly the appearance of slow movements such as those shown in FIG. 3.

The raw eye data may contain three types of eye movement: saccades, pauses, and slow movements. The analysis is performed on the principle that consists in distinguishing these three types of sequential eye data.

Figure 4A:
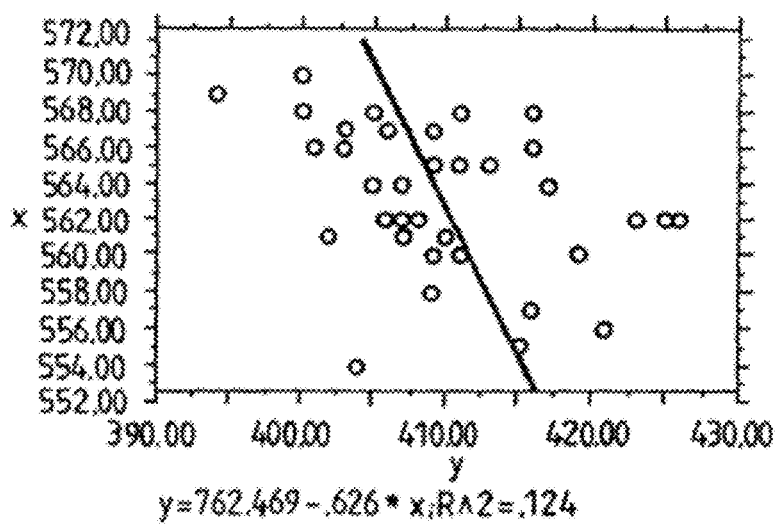
FIG. 4a shows the correlation and the regression slope for a small number of successive coordinates of a slow movement (4a).

Unlike movements in saccades, slow movements are made up of data sequences of values that are close to one another (micro-saccades). This data may be organized in various patterns, for example a segment having a slope, with the slope being determined by linear regression as a function of the relative dispersion of points induced by the succession of micro-saccades (see FIG. 4a on an enlarged scale). Eye pauses comprise data likewise having values that are close together, but that differ because the data does not present the above-described organization as an oriented segment.

The data is analyzed in successive time windows of 500 ms, i.e. 25 data points in each window. A non-supervised training algorithm defines whether two data sets processed as a block do or do not belong to the same class. The non-supervised training consists in identifying classes of elements possessing characteristics that are as similar as possible, and that distinguish the elements from elements of other classes.

Here the elements are data sequences belonging to one of the two classes "slow movements" and "non-slow movements". Since the characteristics of the data are subject to a certain amount of variability and inaccuracy, it is possible to use:

a conventional vector classification method;
a fuzzy classification seeking to process degrees of belonging to imprecisely-defined classes, in association with the use of statistical methods such as analyzing variants (reinforcing results by using a small number of data points that are labeled a priori as "slow movement" or "non-slow movement" in order to be able to use a semi-supervised training method; or
by any other method of classification.

The presence of two classes in succession indicates a saccade.

Figure 4B:
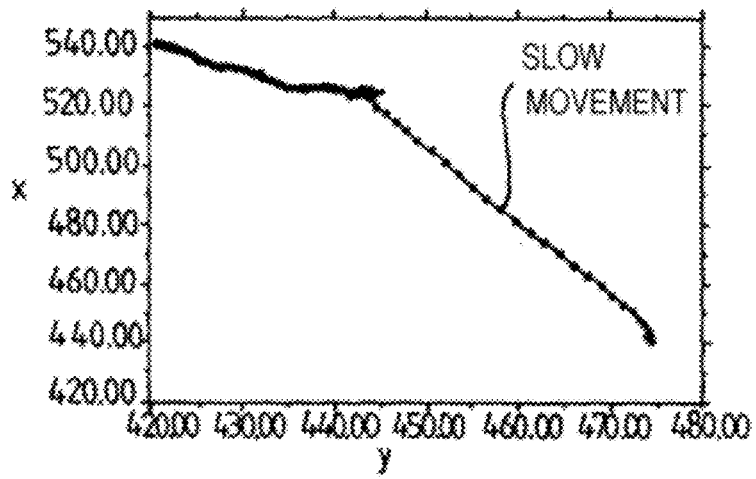
FIG. 4b shows the bivariant function relating to the data that is associated with the slow movements.

Thus, with linear regression, if two data sets correspond to a class, the XY correlation serves to determine the slope of the regression line and to distinguish between an eye pause and a slow movement (FIG. 4b). With a slow movement, processing successive slopes then makes it possible to determine the movement of the camera for two successive groups of points since the direction of the slow movement is known.

Step 3—Corrections Supplied to Camera Movement by the Supervised Training Technique and by Control The adjustments to the speed of movement of the camera are performed by a supervised training technique such as, for example, inductive training by means of a decision tree. It consists in using labeled examples, each example being represented by various characteristics and by a label indicating an action relating thereto. It is performed by determining automatically the pertinence of the characteristics in order to identify the action that is to correspond to a new example of unknown characteristics. This training serves to learn rules that associate eye movement and camera movement. This data is still imprecise (under certain circumstances, several similar movements of the eye can lead to the same movement of the camera), it is preferable to use a fuzzy training method such as for example training by means of a fuzzy decision tree. Since each control can be subjected to settings, the user determines the relationship between the speed of execution of the control and the slow movement of gaze (point 10 in the description of the method). The command transmitted to the camera is corrected on the basis of these parameters.

A fuzzy control method such as the Takagi-Sugeno method based on making use of fuzzy rules (such as those obtained by a fuzzy decision tree) for driving a system on the basis of precise actions (such as those specified in the correspondence table at point 7) enable such correction to be performed automatically.

Other methods that can be used for training and control in fuzzy logic are described for example in the work by B. Bouchon-Meunier and C. Marsala entitled "Traitement de données complexes et commando en logique floue" [Processing complex data and fuzzy logic control] published by Hermes 2003.

The slow movement may be used to perform proportional control: by way of example, the speed of a zoom may be a function of the speed of eye movement. This control may be initiated:

by the slow movement itself; or
by a command (by voice, by manual action on a keyboard, by clicking a mouse, by acting on a joystick, etc., or fixing the gazing on an icon, for example).

Slow movement may also be used in on/off mode to perform a command that has been determined in advance.

Slow movement may be used to select a type of control. By convention, it may be decided that a horizontal movement will control a device to perform traveling, or panning, or indeed a combination of panning and traveling (with the direction and the speed of the movement determining the direction and the speed of the traveling and/or the panning).

The beginning and/or the end of the command may be given respectively by the beginning or the end of the slow movement or by a command given by voice, by eye, or by hand.

Example Application

1. Slow Movements of Real or Virtual 2D or 3D (Relief) Cameras Controlled by Slow Eye Movements Real 2D Cameras A subject being filmed may be tracked while making use of all of the picture-taking axes and of all of the functions of the camera.

The axes are:
for a camera crane: traveling, rising, and swinging the boom arm;
for a head: horizontal rotation (panning), vertical rotation (tilting); and
about the optical axis (rolling);
for a camera having a zoom: zoom, focus, and/or aperture;
for a camera having accessories: compensated variation in the speed of a shutter and/or the aperture (Variospeed); and
in general, any picture-taking function incorporated in the camera menu.

Real 3D (relief) cameras: vergence and spacing between the axes. Servo-controlling any motor-driven or algorithmic effects on the cameras: fading speed, etc.

All of these functions can be controlled by the gaze and they are cumulative, optionally in a hierarchical manner, e.g. by defining the type of control with the help of a command given manually, by eye, or by voice.

Example: tracking a football match with combined panning and traveling movement controlled by slow eye movement.

Prior decision: traveling follows the action at a speed that may be as much as 10 meters per second (m/s) (human running speed) with an angle limit in order to constrain the traveling to follow the action with a panning amplitude of less than 20°, for example. When the operator tracks the ball, the slow eye movement initiates panning. When the panning angle approaches 20° (e.g., 15°), traveling is set automatically into operation so as to return to a position of being perpendicular relative to the longitudinal axis of the pitch.

Virtual 2D and 3D Cameras

All of the functions of real cameras can be applied to virtual cameras.

Using the same mode (combining panning and traveling from a slow eye movement), a spectator can visit a museum or play a video game by moving from room to room. All of the axes may be under servo-control and organized in a hierarchy, with the only limit on spectator movement being constituted by the calculated environment volume (synthesized images).

2. Using Slow Eye Movement to Select One Value from a Plurality or a Continuum of Values Example: Calibration tooling dedicated to post-production. The user selects the point of an image on which work is to be done by gazing. This determines a zone of the image having properties equivalent to the selected point. This zone is then selected. Thereafter, the user gazes on a CIE (Commission Internationale d'Eclairage) chromaticity diagram. As the user's gaze moves, the colors scanned are displayed in the selected zone. An eye command allocates the selection to the zone.

Without losing the image from sight, the user can thus continuously select the value (color or density) that is appropriate.

3. Selection Slow Movement

Example: Selecting Tools

Real Tool

A remote operator with a facility for visual inspection (white rooms) selects various manipulation/work tools for performing actions on articles of differing three-dimensional) natures. A tool suitable for manipulating the article is selected by gaze, fitted to the (controlled) arm, and caused to perform an action.

Detecting that the slow movement of the gaze has stopped consequently serves to select the appropriate type of tool.

Virtual Tool

On the same principle, a player may gain access to instruments of different kinds that are selected by gaze.

4. Combining a Slow Movement with Auxiliary Commands

In the same way that any movement of a real or virtual 2D or 3D camera can be combined as a function of the decision and the hierarchy selected by the operator, the operator may decide at any instant to command the starting or the stopping of a camera movement, or in the middle of a traveling movement, may decide to add a zoom or a change in vergence in the depth of the frame.

Under such circumstances, the command may be manual, i.e. associated with managing an icon, or it may be vocal, thus enabling the user to keep looking at the action.

5. Taking Account of Speed

Example: rotation about the optical axis (roll) in a synthesized image.

Slow tilting (rotation) movement of the head of the user specifies, for the rotation that is performed correspondingly on the screen, simultaneously the direction, the speed, and the acceleration of the resulting rotation. This rotation takes place about the axis passing through the point at which the operator is gazing on the screen and the midpoint between the operator's two eyes.

The movement continues without operator intervention until the moment when the operator decides to stop it.

For a camera, prior to the action, it is possible to select by gaze a certain number of starting and/or ending slow motion images.

6. Controls Associated with Adjusting Relief Settings

The spacing between the camera axes may be increased or reduced as a function of observing a scale or a bar chart after issuing a voice command or identifying an appropriate icon.

Vergence may be generated by visually identifying the convergence plane. This requires a visible reference point to exist.

7. Tracking a Real Scene

Figure 5A:
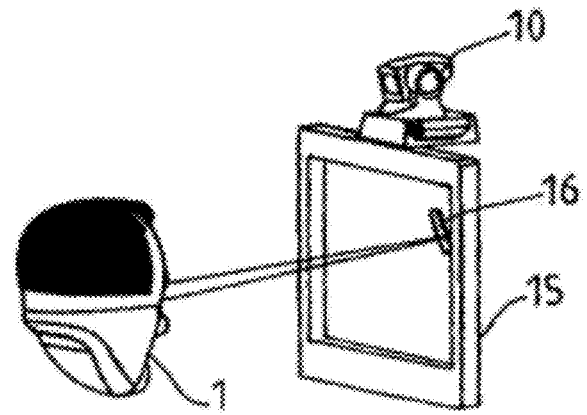
FIGS. 5a and 5b show camera control respectively with the help of a screen or an active-matrix window (5a) or by directly viewing a scene (5b).

The movement of the gaze is detected by an eye tracker.

a. The observer looks at a monitor screen or an active matrix (FIG. 5a).

The gaze may move over the monitor 15 so as to direct the direction in which the controlled camera is pointed in order to view an article 16. Control can thus be applied remotely regardless of the distance involved.

b. The observer looks at a real scene through an active matrix (FIG. 5a).

This example applies to a football match or a play in a theater.

The observed tracks the action by eye through the transparent glass 15 so as to control the camera having parameters that are displayed on the glass (e.g., framing, movement, . . . ). In order to take its shape into account, it is possible to cause a simplified image of the real scene to appear, or in order to take its depth into account it is possible to cause the "Zmap" thereof to appear or indeed a 2D image augmented by depth indices.

Under such circumstances, detecting movements of gaze relates to the subject being filmed.

Figure 5B:
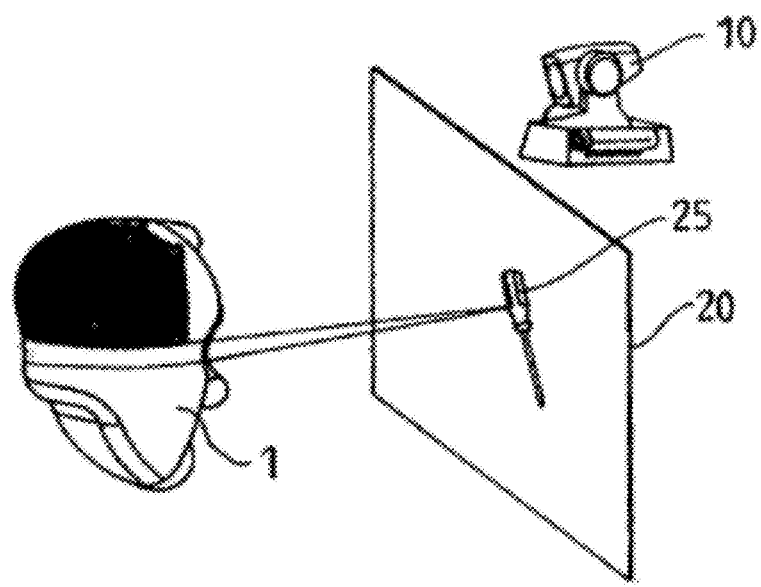

A display system serves to view the foreground, the convergence plane, and the plane at infinity.

c. The observer looks at the real scene without intermediary (FIG. 5b).

Here there is no longer a screen, and the movement of the gaze looking at the real scene 25 is analyzed directly in order to define the framing and the axis of the camera 20. This framing and axis may be viewed in the form of a virtual image.

In addition, an assistant may adjust the focus value, etc., as a function of the scene being tracked by the operator. These adjustments may likewise be controlled by gaze.

The device may thus operate in cascade between a variety of operators, in particular for the operator controlling all or some of the functions of the camera without a screen.

If it is orientation and vergence angle that are detected, it is possible to perform any 2D and 3D control without a screen.

8. An Example of an Application Involving Managing a Tool in Three Dimensions Controlling a robot that moves under gaze control with servo-control functions for a tool that is to be put into position and controlled.

For this type of function, stereoscopy can present a real advantage in manipulating or machining an article of complex surface.

Defecting the three-dimensional shape of the subject being treated and modeling the machine are necessary.

A positioning detector prevents any accidental penetration, and when machining is being performed, the proper distance and angle between the tool and the surface for treatment are known.

The invention claimed is:

1. A control method based on an eye control signal comprising,
   (a) detecting at least one slow movement corresponding to an eye movement of at least one eye of an operator using an eye tracker;
   (b) generating said eye control signal using computer means from at least one detected slow movement; and
   (c) producing a command from the eye control signal, wherein the control method further comprises a training procedure performed with an operator by analyzing eye position data in successive same-duration time windows and by classifying data sets in each window in at least two classes comprising a first class of slow movements, for which a data set comprises sequential data points of values that are close to one another and organized in geometrical shape that is continuous, and a second class of non-slow movements.

2. The method of claim 1, wherein the slow movement corresponds to a regular eye movement of angular speed lying in the range 1°/s to 40°/s.

3. The method of claim 1, wherein detecting the slow movement of the eye comprises determining the path of the eye by a calculation method.

4. The method of claim 1, wherein detecting a saccade and/or a fixed gaze interrupts generation of the eye control signal.

5. The method of claim 1, wherein the eye control signal is a function of eye movement.

6. The method of claim 5, wherein the eye control signal represents the point in three dimensions where the eye is situated and/or the speed of the slow movement of the eye and/or its direction.

7. The method of claim 5, wherein at least one parameter of the eye control signal is a function of at least one parameter of the eye movement.

8. The method of claim 5, wherein producing the command consists of making a choice on a continuum or a choice amongst a discrete number of options, as a function of at least one parameter of the movement of the eye.

9. The method of claim 1, wherein the eye control signal is an on or off signal.

10. The method of claim 1, wherein the type of control to which the eye control signal is allocated is determined by at least one parameter of eye movement.

11. The method of claim 1, wherein the type of control to which the eye control signal is allocated is determined by a command given by voice, by eye, or by hand.

12. The method of claim 1, wherein the beginning and/or the end of the command is generated by the beginning and/or the end of the eye control signal.

13. The method of claim 1, wherein the beginning and/or the end of a command is generated by a command given by voice, by eye, or by hand.

14. The method of claim 1, wherein the method controls the function of a camera.

15. The method of claim 14, wherein the function controlled comprises picture-taking, adjusting zoom, adjusting aperture, adjusting focus, panning, rolling the camera about its own axis, or traveling, or a combination thereof.

16. The method of claim 14, further comprising controlling, by eye, a stereoscopic picture-taking system that includes at least two cameras.

17. The method of claim 16, wherein the method comprises implementing at least one type of control selected from: spacing between axes and/or vergence.

18. The method of claim 1, wherein the class of non-slow movements comprises:
   an eye gaze sub-class comprising data points of values that are close but that are not organized in a symmetrical shape, or
   a sub-class of eye saccades.

19. The method of claim 1, wherein the slow movement corresponds to a regular eye movement of angular speed lying in the range 1°/s to 30°/s.

20. The method of claim 1, wherein the slow movement corresponds to a regular eye movement of angular speed lying in the range 5°/s to 20°/s.

21. The method of claim 3, wherein determining the path of the eye comprises determining the direction of the path.

22. The method of claim 3, wherein the calculation method is linear regression.

23. The method of claim 7, wherein the parameter of the eye movement is speed and/or direction.

24. The method of claim 10, wherein the parameter of eye movement is direction.

* * * * *